(12) United States Patent
Eberler et al.

(10) Patent No.: US 7,719,277 B2
(45) Date of Patent: May 18, 2010

(54) DETECTION UNIT FOR ARRANGEMENT INSIDE A CYLINDRICAL PATIENT RECEPTACLE OF A MAGNETIC RESONANCE APPARATUS

(75) Inventors: Ludwig Eberler, Postbauer-Heng (DE); Razvan Lazar, Erlangen (DE); Jürgen Nistler, Erlangen (DE); Wolfgang Renz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 289 days.

(21) Appl. No.: 11/882,928

(22) Filed: Aug. 7, 2007

(65) Prior Publication Data

US 2008/0068017 A1 Mar. 20, 2008

(30) Foreign Application Priority Data

Aug. 8, 2006 (DE) .................. 10 2006 037 047

(51) Int. Cl.
*G01V 3/00* (2006.01)
(52) U.S. Cl. ...................... 324/318; 324/322
(58) Field of Classification Search .......... 324/318, 324/322, 300
See application file for complete search history.

(56) References Cited

U.S. PATENT DOCUMENTS

| | | | | |
|---|---|---|---|---|
| 4,939,464 A | * | 7/1990 | Hammer | 324/318 |
| 6,060,883 A | * | 5/2000 | Knuttel | 324/318 |
| 7,218,112 B2 | * | 5/2007 | Ladebeck et al. | 324/318 |
| 7,323,874 B2 | * | 1/2008 | Krieg et al. | 324/318 |
| 2008/0137930 A1 | * | 6/2008 | Rosen | 382/131 |

FOREIGN PATENT DOCUMENTS

| | | |
|---|---|---|
| WO | WO 03003038 A1 | 1/2003 |
| WO | WO 2006111869 A2 | 10/2006 |

OTHER PUBLICATIONS

D. Schlyer et al. "Development of a Simultaneous PET/MRI Scanner", Nuclear Science Symposium Conference Record 2004, 16-22. 10.2004, vol. 4, 3419-3421; German Office Action.

* cited by examiner

*Primary Examiner*—Louis M Arana
(74) *Attorney, Agent, or Firm*—Harness, Dickey & Pierce, P.L.C.

(57) ABSTRACT

Detection unit is disclosed for arrangement inside a cylindrical patient receptacle of a magnetic resonance apparatus. In at least one embodiment, the detection unit includes an annular PET detector arrangement with PET detector blocks, and a radiofrequency coil arrangement, arranged coaxially inside the PET detector arrangement and including longitudinal conductors, the longitudinal conductors being guided at least in sections along interspaces between mutually spaced apart detector blocks.

21 Claims, 2 Drawing Sheets

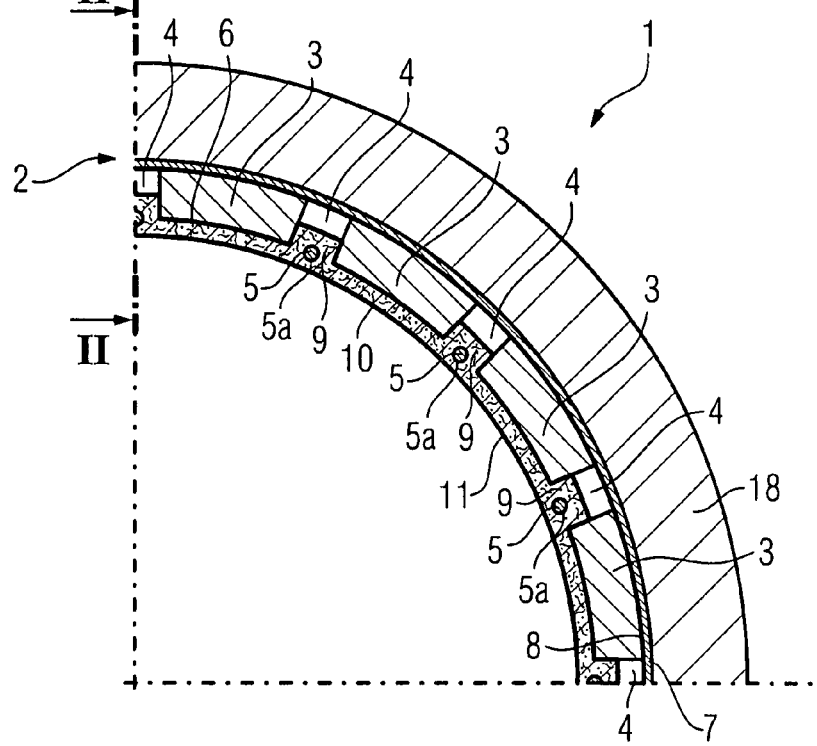
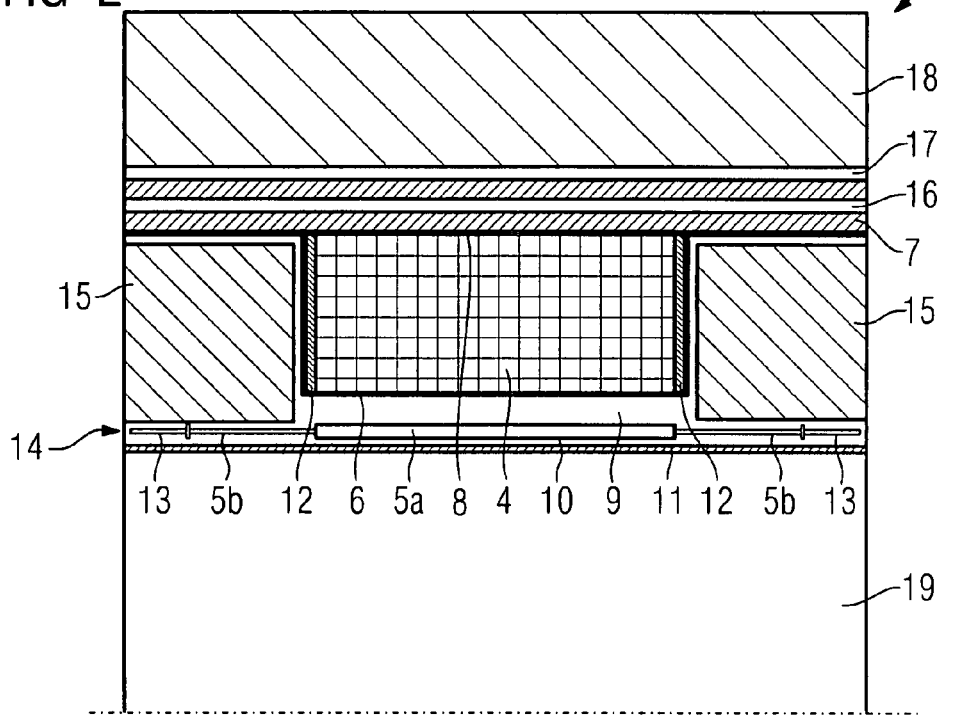

DETECTION UNIT FOR ARRANGEMENT INSIDE A CYLINDRICAL PATIENT RECEPTACLE OF A MAGNETIC RESONANCE APPARATUS

PRIORITY STATEMENT

The present application hereby claims priority under 35 U.S.C. §119 on German patent application number DE 10 2006 037 047.3 filed Aug. 8, 2006, the entire contents of which is hereby incorporated herein by reference.

FIELD

Embodiments of the invention generally relate to a detection unit for arrangement inside a cylindrical patient receptacle of a magnetic resonance apparatus. For example, it may relate to one including an annular PET detector arrangement with PET detector blocks, and a radiofrequency coil arrangement, arranged coaxially inside the PET detector arrangement and having longitudinal conductors.

BACKGROUND

Both magnetic resonance tomography (MRT) and positron emission tomography (PET) are imaging methods that are suitable for displaying the interior of the human body and, particularly in the case of PET, for displaying biochemical processes. There has recently been interest in combining MRT and PET with one another in a unit in order to be able to apply both imaging modalities to the same patient simultaneously or shortly after one another.

It is proposed to this end to provide a possibly removable PET detector additionally inside the magnet arrangement, customary in a magnetic resonance apparatus, composed of basic field magnet and gradient coils. A radiofrequency coil arrangement is to be arranged coaxially for the MRT pictures inside this PET detector arrangement, which is mostly surrounded by a radiofrequency shield.

Both imaging methods, and thus both arrangements share the same isocentric region, that is to say both the PET detector arrangement and the radiofrequency coil arrangement require the same isocentric space in the plane perpendicular to the longitudinal axis of the magnetic resonance apparatus, which is frequently also denoted as the Z-axis, the isocenter being located at Z=0.

To this end, it has been proposed to arrange the PET detector arrangement inside the patient receptacle of the magnet of the magnetic resonance apparatus, the radiofrequency coil arrangement, in turn, being inserted into the annular PET detector arrangement. However, a few problems arise in this case. Firstly, the radiofrequency coils and the PET detectors interfere mutually with one another, since the currents generate inside the PET detector arrangement interference fields that can be captured by the radiofrequency coil and possibly lead to interference signals. In order to avoid this interference, it is proposed to provide a radiofrequency shield at least between the radiofrequency coil arrangement and the PET detector arrangement, such that the respective interference fields are shielded against one another. In this case, the entire PET detector arrangement can also be surrounded by such a radiofrequency shield in the manner of a Faraday cage.

A further problem is that the patient receptacle is extremely reduced in the case of such a design of onion-skin type. The inside diameter of the radiofrequency coil arrangement remaining for the patient is then very small, and so psychological effects such as, for example, claustrophobia, and problems based on a high body volume can greatly stress the patient by reducing comfort.

If such a radiofrequency shield is provided, the problem is additional rendered more acute by virtue of the fact that the conductors of the radiofrequency coil arrangement can no longer be arranged directly in the vicinity of this radiofrequency shield, since a certain reverse field flux space is required for the field lines of the radiofrequency field to be able to close. Consequently, the conductors of the radiofrequency coil arrangement should exhibit a certain distance from a radiofrequency shield, and this leads to a further constriction of the space that remains for the patient.

SUMMARY

In at least one embodiment of the invention, a detection unit is disclosed, by which it is possible to implement a larger patient opening.

According to at least one embodiment of the invention, longitudinal conductors are guided at least in sections along interspaces between mutually spaced apart detector blocks.

The PET detector arrangement is constructed from a number of PET detector blocks that, for example, respectively comprise a crystal block made from LSO, a photodiode and the corresponding electronics. If interspaces are now present between these individual detector blocks, particularly in an axial direction, the longitudinal conductors of the radiofrequency coil arrangement can advantageously be guided along these interspaces, that is to say their course follows the course of these interspaces. This enables a geometrically optimized integration of the PET detector arrangement with the radiofrequency coil arrangement while requiring the same isocentric space region.

Such an integrated design of interwoven systems additionally enables a cost-optimized production. It is therefore possible to use the detection unit of at least one embodiment of the invention without any problem to record the same volume synchronously or consecutively, that is to say MRT and PET examinations can take place by way of the same device, in particular at the same time.

The detector arrangement is usually provided at least on the radiofrequency coil side with a radiofrequency shield that advantageously prevents interference fields from being able to be responsible for mutual influence between the two arrangements. If the radiofrequency shield is provided directly on the surface of the PET detector arrangement facing the radiofrequency coil arrangement, the interspaces advantageously form reverse field flux spaces in the case of the inventive arrangement of the longitudinal conductors. The interspaces are then used not only for a geometrically optimized design, but additionally serve as a reverse field flux space.

The interspaces can advantageously form a depression that is continuous in an axial direction, that is to say an interspace running continuously in an axial direction is present, or the interspaces are arranged aligned in an axial direction. The corresponding section of the longitudinal conductor can then be guided in a straight path along the interspaces.

The exact arrangement of the longitudinal conductors, in particular the radius at which they run, is largely determined by the presence and the distance of a radiofrequency shield. In order for an adequate reverse field flux space to be present, and for an adequate quality of the radiofrequency field and thus of the pictures to be achieved, there is a need for a certain distance in order to form this reverse field flux space. There are then two cases to be distinguished here, in the final analysis.

In an example embodiment, it can be provided that the longitudinal conductors are guided inside the interspaces at least over a portion of their radial cross section, preferably over its entirety. In this embodiment, the longitudinal conductors of the radiofrequency coil arrangement are geometrically completely integrated in the PET detector arrangement, and thus the relevant radial dimensions are determined here in the final analysis by the PET detector arrangement. This configuration is enabled above all whenever there is nevertheless an adequate distance from the radiofrequency shield owing to the interspaces. If, as already described, the radiofrequency shield is attached directly on the surface of the PET detector arrangement on the radiofrequency coil side, the interspaces themselves form the complete reverse field flux space, in the final analysis.

In another embodiment, it is possible for the longitudinal conductors to be guided above the interspaces. Something of this sort can, for example, turn out to be necessary whenever a relatively large distance from the radiofrequency shield is required. Thus, for example, the indentations resulting from the interspaces can, when they are coated with a radiofrequency shield, fail to be deep enough should the interspaces simultaneously be used to accommodate electronic components of the PET detector blocks, for example, in the region facing outward. Nevertheless, the result here overall is a detector unit that is narrower in a radial direction, since it is possible owing to the indentations for the longitudinal conductors to be provided further to the outside without falling short of the required distance from a radiofrequency shield.

The longitudinal conductors are expediently guided in the middle with reference to the interspaces. Thus, an equal distance of the longitudinal conductor to either side of the lateral surface of the interspaces is provided. The longitudinal conductor is therefore arranged in the middle between the two sides. If the longitudinal conductors are guided inside the interspaces, it is also advantageously possible for the minimum distance from the bottom of the interspaces to correspond to the minimum distance from the lateral boundaries of the interspaces. A uniform reverse field flux space of symmetrical design is thereby provided in the case of surfaces of the interspace that are covered by the radiofrequency shield.

At least the sections of the longitudinal conductors that are guided along the interspaces can expediently be designed as wires with a preferably round cross section. By contrast with the conventional design as flat conductors, in particular made from copper foil, the wire-type design of the longitudinal conductors provides the possibility that the corresponding sections of the longitudinal conductors have as large as possible a distance from the detector blocks inside the interspace as well, in particular from a radiofrequency shield covering these. The diameter of the wires should be, in particular, at least 4 mm. The round design is not mandatory here; it can also be provided that the longitudinal conductors only become narrower in the immediate vicinity of the PET detector blocks.

In order to achieve an adequate extent of the reverse field flux space, it can be provided that the wires are spaced apart from a radiofrequency shield, shielding the radiofrequency coil arrangement from the PET detector arrangement, at least by their diameter, preferably by 5 to 10 times their diameter. A high quality of the radiofrequency field, and thus of the resulting pictures is achieved by this adequate distance. The coherent radiofrequency shield of the PET detector arrangement still serves in this case, as reverse current surface for the radiofrequency currents.

In particular, the radiofrequency coil arrangement can also be designed as a so-called birdcage coil. In this case, two conducting end rings whose midpoint is formed by the longitudinal axis are connected by axially running longitudinal conductors. In such an arrangement, the end rings can be arranged upstream and downstream of the detector arrangement in an axial direction. Consequently, a larger reverse field flux space is fundamentally available in the outer regions of the coil. The end rings thus run overall outside the PET detector arrangement through which the longitudinal conductors are guided, at least in sections, along and/or in the interspaces. Of course, it is also conceivable likewise to integrate the end rings geometrically in the PET detector arrangement by using azimuthally running interspaces. However, it is then necessary to reckon with a smaller reverse field flux space.

Customary PET detector arrangements used have a length of approximately 20 to 30 cm, while a coil serving as body coil, for example, can exhibit a length of up to 50 cm. The PET detector is in this case arranged centrally, the two end rings run outside the interspaces, and the longitudinal conductors run inside, as described.

In the case of such an arrangement, where the end rings are located upstream and downstream of the PET detector arrangement, it is particularly advantageously possible that the end rings and/or sections of the longitudinal conductors that do not run inside the detector arrangement are designed as flat conductors, in particular made from copper foil. High-quality radiofrequency fields are produced with the aid of such a conductor structure, particularly in the mainly relevant end ring region. Of course, it is also conceivable to design the longitudinal conductors in the shape of wires over their entire length such that simpler production is possible. A mix structure of the longitudinal conductors, which are designed as flat conductors in the regions adjoining the end rings, and as wires in the region of the interspaces, is also, however, possible. Finally, an embodiment would be conceivable in which the longitudinal conductors are designed in a wire-type fashion over the entire length, in particular being of round design, there being an outward widening to a larger diameter in a stepped or conical fashion.

Furthermore, the end rings arranged upstream and downstream of the detector arrangement in an axial direction can be arranged on spacers, in particular made from foam plastic, that essentially exhibit the dimensions of the detector arrangement in a radial direction, and serve as reverse field flux space. In this case, the end rings expediently have a radius that also corresponds to that of the longitudinal conductor structure, an annular radiofrequency coil arrangement thereby being provided. The spacers not only hold the end rings: a reverse field flux space is simultaneously provided that is of adequate size in these regions in which, in particular, current flows through. The minimum thickness of the reverse field flux space in the region of the end rings should, however, not substantially fall below 30 to 40 mm, this having to be borne in mind, in particular, when, for example, connecting cables for the radiofrequency coil or the PET detector arrangement are likewise guided through this region.

In the case of such a structure of the radiofrequency coil arrangement where all the conductor elements lie on the same radius, the end ring sections in the inventive detection unit are therefore also further removed from the patient so that, on the one hand, there is more room and, on the other hand, an SAR optimization (SAR=Specific Absorption Rate) is possible.

A number of possibilities are conceivable for holding the sections of the longitudinal conductors that are guided along the interspaces. Thus, in one embodiment of the invention, the sections of the longitudinal conductors that are guided along the interspaces can be held by way of a dielectric material filling up the interspaces, in particular can be cast into said material. The longitudinal conductor sections thus become an integral constituent of the overall arrangement, there being only a slight risk of subsequent displacement.

Alternatively, it is also conceivable, of course, that at least the sections of the longitudinal conductors that are guided along the interspaces are held by way of holder elements, in particular made from Teflon. Continuous holding is thereby conceivable just as is punctiform holding. The overall holding design can be fastened in the end ring region or, for example, on an inner covering of the detection unit.

The inventive detection unit of at least one embodiment can in this case be both a mobile unit that is inserted into a magnetic resonance apparatus only when required, or a detection unit that is permanently installed inside a magnetic resonance apparatus. In the case of mobile units, both a whole body detection unit and a head detection unit are conceivable. The dimensioning of the detection unit is also to be designed as a function thereof.

The detection unit of at least one embodiment can expediently have a support tube on whose inside the PET detector arrangement and, if appropriate, the radiofrequency coil arrangement are fastened. Consequently, the support tube surrounds the PET detector arrangement and the radiofrequency coil arrangement to the outside and can, in the case of a detection unit that is mobile and/or can be removed for maintenance purposes, also by way of example include at least one guide device(s) with the aid of which the detection unit can conveniently be guided inside the patient receptacle through interaction with at least one guide device(s) on the magnetic resonance apparatus side. In addition, such a support tube can also serve for holding the arrangements located in it.

The PET detector arrangement is fastened directly on the support tube in this case. A number of possibilities are conceivable for fastening the radiofrequency coil arrangement. Thus, said arrangement can likewise be fastened on the support tube via appropriate holder elements, in particular also by way of the spacers, but it is also possible to conceive of fastening on the PET detector arrangement. Furthermore, it is conceivable to attach the radiofrequency coil arrangement on an inner covering that, in turn, can be held on the support tube.

In an advantageous refinement, the connecting cables of the PET detector arrangement and/or of the radiofrequency coil arrangement can be integrated in the support tube. In this case, there is provided inside the support tube a cutout through which the appropriate cabling is guided. Alternatively or additionally it is also possible for a cooling system for cooling the PET detector arrangement and/or the radiofrequency coil arrangement to be integrated in the support tube. Such a cooling system can also be arranged in cavities or cutouts inside the support tube. To the effect of further reducing the inside diameter of the detection unit, the support tube is therefore also used to accommodate elements of the detection unit integratively such that these require no additional space in a radial direction.

The PET detector arrangement can expediently be provided with annular shielding elements on its end faces. The elements are as opaque as possible to gamma radiation, and thus effect shielding against scattered radiation from outside the PET detector arrangement.

As already mentioned, the detection unit can be closed inwardly by an inner covering. By way of example, the radiofrequency coil arrangement can also be fastened on such an inner covering. It serves, in addition, to protect the components and to provide an optimized optical configuration.

In addition, at least one embodiment of the invention also relates to a magnetic resonance apparatus comprising a cylindrical basic field magnet and one or more gradient coils arranged inside the basic field magnet, the magnetic resonance apparatus comprising an inventive detection unit fastened inside the gradient coil. Such a detection unit thus forms an integral part of a magnetic resonance apparatus that is suitable for recording PET and MRT pictures. Of course, a larger patient receptacle is also possible here, in particular.

BRIEF DESCRIPTION OF THE DRAWINGS

Further advantages and details of the invention emerge from the example embodiments described below, as well as with the aid of the drawings, in which:

FIG. 1 shows a cross section of a quarter of the circumference of a detection unit inserted in accordance with an embodiment of the present invention in a magnetic resonance apparatus, FIG. 2 shows a longitudinal section along the line II-II in FIG. 1.

DETAILED DESCRIPTION OF THE EXAMPLE EMBODIMENTS

Figure 3:
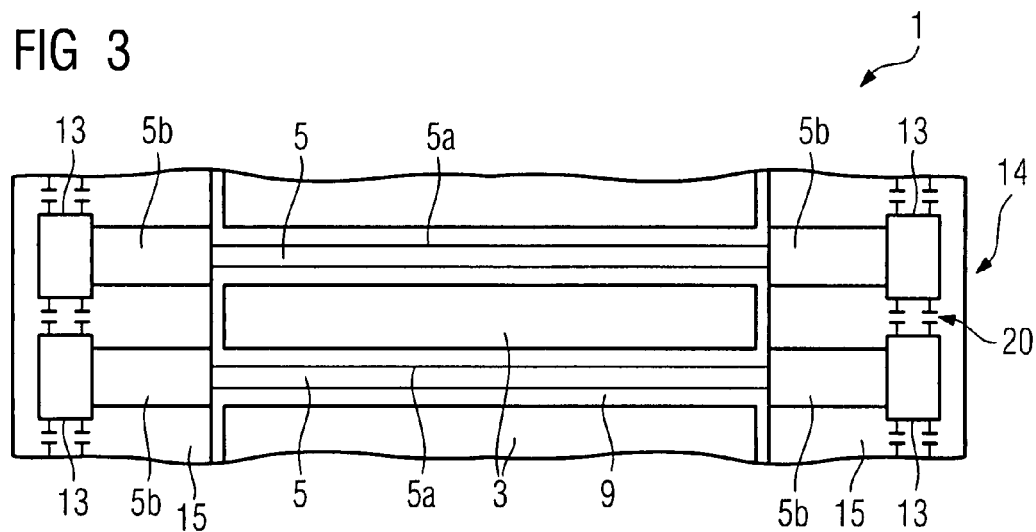
FIG. 3 shows a plan view of the radiofrequency coil arrangement of the detection unit from FIGS. 1 and 2.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows a cross section through a detection unit 1 inserted inside the gradient coils 18 into the patient receptacle 19 in a magnetic resonance apparatus, only a quarter of the total circumference being shown here, for the sake of clarity. The detection unit 1 comprises a PET detector arrangement 2 that comprises detector blocks 3 and electronics 4 arranged between the detector blocks. The PET detector arrangement 2 is shielded by a radiofrequency shield 6 from a radiofrequency coil arrangement, of which here only the longitudinal conductors 5 are illustrated. The PET detector arrangement 2 and the radiofrequency coil arrangement are surrounded by a support tube 7 on which the PET detector arrangement is fastened. A radiofrequency shield 8 is also provided between the support tube 7 and the PET detector arrangement 2.

The connecting cables of the PET detector arrangement and of the radiofrequency coil arrangement, as well as a cooling system for cooling the PET detector arrangement 2 and the radiofrequency coil arrangement are integrated in the support tube 7—which is not shown in more detail here.

As may be seen in FIG. 1, the PET detector blocks 3 are arranged spaced apart from one another in an azimuthal direction, and are higher than the electronics 4, such that interspaces 9 in the form of indentations result. Guided inside these interspaces 9 are sections 5a of the longitudinal conductors 5 of the radiofrequency coil arrangement that have a round cross section and are of wire-type design. The diameter of the longitudinal conductors is 4 mm in this example. The longitudinal conductors 5 are arranged in the middle of the interspaces 9 in an azimuthal direction such that they are at the same distance from the side walls of the interspaces and the base of the interspaces, which distance is greater than their diameter. Since the surface of the interspaces 9 is provided with the radiofrequency shield 6, the longitudinal conductors 5 are also adequately spaced apart therefrom, although they do not protrude beyond the detector arrangement 2. The interspaces 9 act as reverse field flux space, while the radiofrequency shield 6 acts as reverse current surface. According to the invention, a perfect geometric integration is therefore present such that the inside diameter of the detector unit is significantly increased.

The wire-shaped longitudinal conductor sections 5a are held at their position in the interspaces 9 by way of a dielectric material 10 into which they are cast. The dielectric material 10 can be a transparent resin, for example. Alternatively, it is also conceivable that the sections 5a of the longitudinal conductors 5 are guided in holders.

The detector unit 1 can optionally be covered inwardly by an inner covering 11.

FIG. 2 shows a longitudinal section along the line II-II from FIG. 1 through the detection unit 1. An electronics region 4 of the detector arrangement 2 is to be seen centrally. Extending inward is the interspace 9. The round section 5a, of wire-type design, of the longitudinal conductor 5, which is made from copper for example, is guided in this interspace 9. In an axial direction upstream and downstream of the detector arrangement 2, the longitudinal conductor 5 continues in further sections 5b, which are designed as flat conductors, here made from copper foil, and adjoin end rings 13. The longitudinal conductors 5 with the sections 5a and 5b, and the end rings 13 form the radiofrequency coil arrangement 14, which is designed here in the manner of a birdcage coil. Whereas the section 5a, running in the interspaces 9, of the longitudinal conductor 5 is held by the dielectric material 10, the flat conductors of the sections 5b and of the end rings 13 are arranged on spacers 15 consisting of foam plastic. The radiofrequency shield 6 may be seen to continue laterally up to the edge of the detector unit 1 at the support tube 7, such that the spacers 15 form a reverse field flux space of adequate size in the region of the end rings 13.

As may likewise be seen from FIG. 2, a cooling system 16 for cooling the PET detector arrangement 2 and the radiofrequency coil arrangement 14, and the connecting cables 17 of the PET detector arrangement 2 and the radiofrequency coil arrangement 14 are integrated in the support tube 7.

At the side, the detector arrangement 2 is, moreover, delimited by annular shielding elements 12. These are as far as possible opaque to gamma rays and thus effect shielding against scattered radiation from outside the PET detectors 3.

The detector unit is, in turn, inserted into the magnetic resonance apparatus in a fashion directly adjoining the gradient coils 18. An inner covering 11 can optionally be provided toward the patient receptacle 19.

FIG. 3 shows a plan view of the inside of the detection unit 1. The birdcage structure of the radiofrequency coil arrangement 14 is well in evidence. Two end rings 13 with appropriate resonance capacitors 20 are connected by the longitudinal conductors 5, which are designed in wire-type fashion in the sections 5a running inside the interspaces 9 between the detector blocks 3, but as flat conductors outside the interspaces 9 in the sections 5b.

Figure 4:
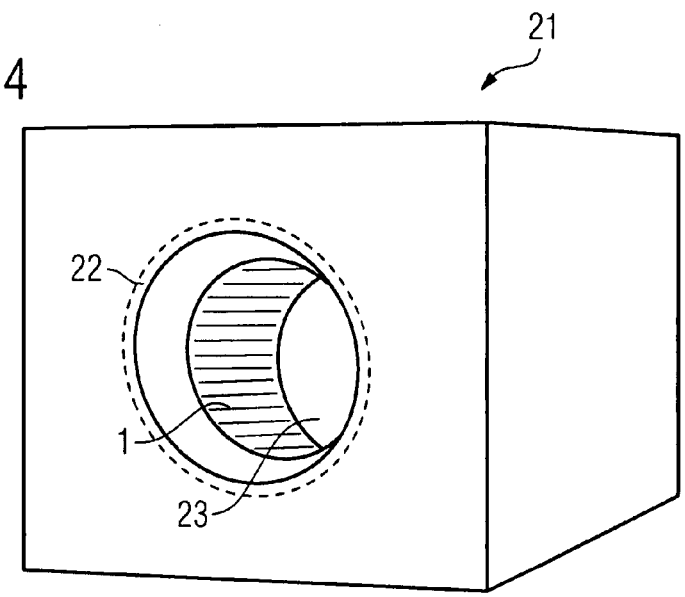
FIG. 4 shows an inventive magnetic resonance apparatus.

Finally, FIG. 4 shows an inventive magnetic resonance apparatus 21. It may be seen that a detection unit 1 that defines the patient receptacle 23 is fastened inside the gradient coils 22.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detection unit for arrangement inside a cylindrical patient receptacle of a magnetic resonance apparatus, comprising:
    an annular positron emission tomography (PET) detector arrangement including mutually spaced apart PET detector blocks and interspaces between the PET detector blocks; and
    a radiofrequency coil arrangement, arranged coaxially inside the PET detector arrangement and including longitudinal conductors, the longitudinal conductors being guided at least in sections inside the interspaces at a distance apart from a surface of the interspaces.

2. The detection unit as claimed in claim 1, wherein the longitudinal conductors are guided inside the interspaces at least over a portion of their radial cross section.

3. The detection unit as claimed in claim 1, wherein the longitudinal conductors are guided in the middle with reference to the interspaces.

4. The detection unit as claimed in claim 1, wherein at least the sections of the longitudinal conductors that are guided inside the interspaces are designed as wires with a preferably round cross section and having a diameter that is at least 4 mm.

5. The detection unit as claimed in claim 4, wherein the wires are spaced apart from a radiofrequency shield, shielding the radiofrequency coil arrangement from the PET detector arrangement, at least by their diameter.

6. The detection unit as claimed in claim 1, wherein, in the case of a radiofrequency coil arrangement designed as a birdcage and having two end rings connected by the longitudinal conductors, the end rings are arranged upstream and downstream of the detector arrangement in an axial direction.

7. The detection unit as claimed in claim 6, wherein at least one of the end rings and sections of the longitudinal conductors that do not run inside the detector arrangement are designed as flat conductors.

8. The detection unit as claimed in claim 6, wherein the end rings are arranged on spacers that essentially exhibit the dimensions of the detector arrangement in a radial direction, and serve as reverse field flux space.

9. The detection unit as claimed in claim 1, wherein at least the sections of the longitudinal conductors that are guided inside the interspaces are held by way of a dielectric material filling up the interspaces.

10. The detection unit as claimed in claim 1, wherein at least the sections of the longitudinal conductors that are guided inside the interspaces are held by way of holder elements.

11. The detection unit as claimed in claim 1, further comprising:
a support tube inside the PET detector arrangement to which the radiofrequency coil arrangement is fastened.

12. The detection unit as claimed in claim 11, wherein the connecting cables of at least one of the PET detector arrangement and the radiofrequency coil arrangement are integrated in the support tube.

13. The detection unit as claimed in claim 11, wherein a cooling system for cooling at least one of the PET detector arrangement and the radiofrequency coil arrangement is integrated in the support tube.

14. The detection unit as claimed in claim 1, wherein the PET detector arrangement is provided with annular shielding elements on its end faces.

15. The detection unit as claimed in claim 1, wherein the detection unit is closed inwardly by an inner covering.

16. A magnetic resonance apparatus, comprising:
a cylindrical basic field magnet;
one or more gradient coils arranged inside the cylindrical basic field magnet; and
a detection unit, fastened inside the one or more gradient coils, as claimed in claim 1.

17. The detection unit as claimed in claim 1, wherein the longitudinal conductors are guided inside the interspaces over the entirety of their radial cross section.

18. The detection unit as claimed in claim 2, wherein the longitudinal conductors are guided in the middle with reference to the interspaces.

19. The detection unit as claimed in claim 17, wherein the longitudinal conductors are guided in the middle with reference to the interspaces.

20. The detection unit as claimed in claim 4, wherein the at least the sections of the longitudinal conductors that are guided inside the inter-spaces are designed as wires with a round cross section and having a diameter that is at least 4 mm.

21. The detection unit as claimed in claim 12, wherein a cooling system for cooling at least one of the PET detector arrangement and the radiofrequency coil arrangement is integrated in the support tube.

* * * * *